（12) United States Patent
Nikoozadeh et al.

(10) Patent No.: US 9,678,591 B2
(45) Date of Patent: Jun. 13, 2017

(54) METHOD AND APPARATUS FOR SENSING TOUCH

(71) Applicant: The Board of Trustees of the Leland Stanford Junior University, Palo Alto, CA (US)

(72) Inventors: Amin Nikoozadeh, Palo Alto, CA (US); Butrus T. Khuri-Yakub, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 49 days.

(21) Appl. No.: 14/300,033

(22) Filed: Jun. 9, 2014

(65) Prior Publication Data

US 2014/0362013 A1   Dec. 11, 2014

Related U.S. Application Data

(60) Provisional application No. 61/833,327, filed on Jun. 10, 2013.

(51) Int. Cl.
*G06F 3/041* (2006.01)
*G06K 9/00* (2006.01)
*G06F 21/32* (2013.01)
*G06K 19/07* (2006.01)
*A61B 5/1172* (2016.01)
*G06F 3/044* (2006.01)
*A61B 5/021* (2006.01)
*A61B 5/024* (2006.01)

(52) U.S. Cl.
CPC .......... *G06F 3/0414* (2013.01); *A61B 5/1172* (2013.01); *G06F 3/044* (2013.01); *G06F 21/32* (2013.01); *G06K 9/0002* (2013.01); *G06K 19/07* (2013.01); *A61B 5/021* (2013.01); *A61B 5/024* (2013.01); *A61B 2562/0247* (2013.01); *A61B 2562/046* (2013.01)

(58) Field of Classification Search
None
See application file for complete search history.

(56) References Cited

U.S. PATENT DOCUMENTS

| 5,325,442 | A | * | 6/1994 | Knapp | ............... G01B 7/004 361/278 |
| 5,889,236 | A | | 3/1999 | Gillespie et al. | |
| 5,943,043 | A | | 8/1999 | Furuhata et al. | |
| 6,222,528 | B1 | | 4/2001 | Gerpheide et al. | |

(Continued)

OTHER PUBLICATIONS

J. Pennack and M.H.N. Tabrizi, "A Survey of Input Sensing and Processing Techniques for Multi-Touch Systems." Proceedings of the 2008 International Conference on Computer Design, CDES 2008, Las Vegas, Jul. 14-17, 2008.

*Primary Examiner* — Dismery Mercedes
(74) *Attorney, Agent, or Firm* — Crawford Maunu PLLC

(57) ABSTRACT

Aspects of the present disclosure are directed towards methods, systems, and apparatuses that include a pressure-sensor arrangement including a plate structure and a plurality or array of pressure-sensor cells. Additionally, the methods, systems, and apparatuses include integrated circuitry communicatively coupled to the pressure-sensor arrangement that senses pressure changes exhibited by changes in capacitance or vibrational characteristics.

20 Claims, 3 Drawing Sheets

(56) References Cited

U.S. PATENT DOCUMENTS

| | | | |
|---|---|---|---|
| 6,408,087 B1 * | 6/2002 | Kramer | G06F 3/03547 345/156 |
| 6,578,436 B1 * | 6/2003 | Ganapathi | G06K 9/0002 73/862.046 |
| 6,633,656 B1 * | 10/2003 | Picard | G06K 9/0002 340/5.53 |
| 6,829,950 B2 * | 12/2004 | Ganapathi | G06K 9/0002 73/862.046 |
| 7,135,645 B2 | 11/2006 | Hiraki et al. | |
| 7,278,025 B2 | 10/2007 | Saito et al. | |
| 7,331,245 B2 | 2/2008 | Nishimura et al. | |
| 7,437,953 B2 * | 10/2008 | DeConde | G06K 9/0002 73/862.042 |
| 8,076,949 B1 | 12/2011 | Best et al. | |
| 8,279,180 B2 | 10/2012 | Hotelling et al. | |
| 8,296,573 B2 | 10/2012 | Bolle et al. | |
| 8,363,020 B2 | 1/2013 | Li et al. | |
| 8,390,411 B2 | 3/2013 | Lauder et al. | |
| 8,402,831 B2 * | 3/2013 | Kupnik | B06B 1/0292 310/300 |
| 8,416,209 B2 | 4/2013 | Hotelling et al. | |
| 8,432,371 B2 | 4/2013 | Hotelling et al. | |
| 2003/0215976 A1 * | 11/2003 | Chou | G06K 9/0002 438/57 |
| 2004/0129787 A1 | 7/2004 | Saito et al. | |
| 2005/0124864 A1 * | 6/2005 | Mack | A61B 5/024 600/300 |
| 2006/0279548 A1 | 12/2006 | Geaghan | |
| 2008/0056543 A1 * | 3/2008 | Morimura | A61B 5/1172 382/124 |
| 2008/0199058 A1 * | 8/2008 | Chou | G06K 9/00013 382/125 |
| 2009/0051671 A1 | 2/2009 | Konstas | |
| 2011/0031566 A1 * | 2/2011 | Kim | B81C 1/00158 257/419 |
| 2011/0043077 A1 * | 2/2011 | Yeh | F03G 7/005 310/338 |
| 2011/0181552 A1 | 7/2011 | Goertz et al. | |
| 2011/0254108 A1 * | 10/2011 | Gozzini | G06K 9/00053 257/415 |
| 2012/0092350 A1 * | 4/2012 | Ganapathi | G02B 26/0833 345/501 |
| 2012/0134549 A1 * | 5/2012 | Benkley, III | G01N 27/04 382/124 |
| 2012/0253205 A1 * | 10/2012 | Cho | A61B 5/6843 600/479 |
| 2013/0287274 A1 * | 10/2013 | Shi | G06F 3/044 382/124 |
| 2014/0049703 A1 * | 2/2014 | Hu | G02F 1/13338 349/12 |
| 2014/0159746 A1 * | 6/2014 | Lu | G06F 3/044 324/658 |
| 2014/0333328 A1 * | 11/2014 | Nelson | G06F 3/044 324/663 |

* cited by examiner

METHOD AND APPARATUS FOR SENSING TOUCH

BACKGROUND

Touch sensors are widely used in many devices such as smart phones, tablets, laptops, etc. Touch sensors are also applicable in authentication (e.g., fingerprint scanning) Consumer electronics can include methods for authentication that enables conveniently accessed sensitive information (e.g., bank accounts) on these portable devices without entering a password. As a result, there is a need for a low-power reliable authentication method that can be integrated for example in smart phones and tablets.

These and other matters have presented challenges to transistor devices, for a variety of applications.

SUMMARY

Various aspects of the present disclosure are directed toward an array of pressure sensors. Utilizing pressure sensing technology can provide for low-power and reliable touch determination and authentication in a wide variety of devices such as smart phones and tablets. This enables convenient and secure access to sensitive information (e.g., bank accounts) on portable devices without entering a password, and also allows for determining touch on a touch screen. Aspects of the present disclosure are believed to be applicable to a variety of different types of devices, systems and arrangements involving touch sensors.

Various aspects of the present disclosure are directed towards methods, systems, and apparatuses that include a pressure-sensor arrangement including a plate structure and a plurality or array of pressure-sensor cells. Additionally, the methods, systems, and apparatuses include integrated circuitry communicatively coupled to the pressure-sensor arrangement that senses pressure changes exhibited by changes in capacitance or vibrational characteristics. The plurality of pressure-sensor cells and the plate structure provide different changes in capacitance or vibrational characteristics, via the separate signal paths, in response to a touch event at or near the plate structure as caused by a single touch implement.

The above discussion/summary is not intended to describe each embodiment or every implementation of the present disclosure. The figures and detailed description that follow also exemplify various embodiments.

BRIEF DESCRIPTION OF THE FIGURES

Various example embodiments may be more completely understood in consideration of the following detailed description in connection with the accompanying drawings, in which.

Figure 1:
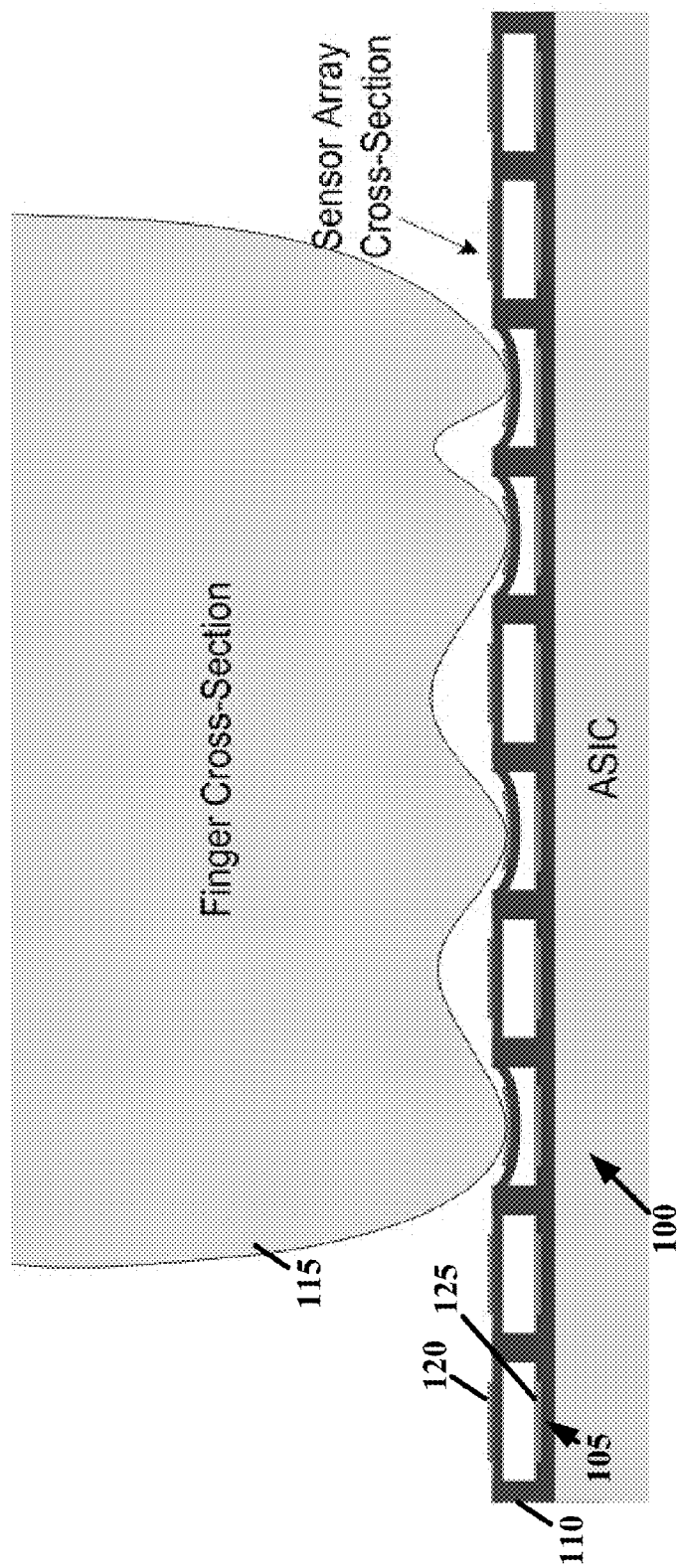
FIG. 1 shows an example pressure-sensor array, consistent with various aspects of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Various aspects of the present disclosure are directed toward pressure sensors, including arrays of pressure sensors. Each pressure sensor includes a flexible plate anchored around edges of the sensor. In response to the application of a pressure (e.g., touch) the flexible plate deflects, and this deflection is detected. Utilizing an array of pressure sensors, consistent with various aspects of the present disclosure, enables a multitude of different types of detection and functionalities. For instance, an array of the pressure sensors can be provided in a touch screen apparatus such that the array of pressure sensors will determine touch location. Additionally, the array of pressure sensors can be utilized as a fingerprint scanner apparatus.

Aspects of the present disclosure are directed towards methods, systems, and apparatuses that include a pressure-sensor arrangement including a plate structure and a plurality or array of pressure-sensor cells. Additionally, the methods, systems, and apparatuses include integrated circuitry communicatively coupled to the pressure-sensor arrangement that senses pressure changes exhibited by changes in capacitance or vibrational characteristics. The plurality of pressure-sensor cells and the plate structure can provide different changes in capacitance or vibrational characteristics, via the separate signal paths, in response to a touch event at or near the plate structure as caused by a single touch implement. In certain specific embodiments, the pressure-sensor arrangement includes at least three pressure-sensor cells. Additionally, the separate signal paths for each of the respective pressure-sensor cells provides an indication of a change in pressure in response to the touch event at or near the plate structure as caused by the single touch implement. In certain embodiments, the pressure-sensor arrangement includes several pressure-sensor cells and the separate signal paths for each of the respective pressure-sensor cells provides an indication of a change in pressure in response to the touch event at or near the plate structure in order to sense a plurality of ridges in the touching implement (such as a finger).

Certain embodiments of the present disclosure can also include a touch screen in which the plate structure deflects in response to the touch event. In certain embodiments, the touch screen and the plate structure deflect in response to the touch event, and the pressure-sensor arrangement can detect sufficient ridges in a fingerprint for differentiating between ridge spacing along at least one direction. Additionally, in other embodiments, the pressure-sensor arrangement can detect sufficient ridges in a fingerprint for differentiating between ridge spacing along at least two directions. The apparatuses, methods, and systems can also include a touch surface provided over the plurality of pressure-sensor cells and the plate structure. The touch surface is provided across an area that is at least sufficient to allow a single touch implement, such as multiple fingers or a user's palm, to contact the touch surface.

The single touch implement described herein can also be a stylus. Further, the stylus can have a plurality of surface irregularities at the tip. In certain embodiments, the pressure-sensor arrangement utilizes the separate signal paths such that each of the respective pressure-sensor cells provides an indication of a change in pressure in response to the touch event, at or near the plate structure in order to sense different ones of the plurality of surface irregularities of the stylus. In other embodiments, the single touch implement is a finger of a user. In these such embodiments, the changes in capacitance or vibration characteristics are indicative of one or more of heart rate, breathing rate and temperature of the user, or indicative of blood flow of the user. Further, the changes in capacitance or vibration characteristics can be indicative of tracks of blood vessels of the finger.

Additionally, in certain embodiments of the present disclosure, the single touch implement is a finger of a user. Further, the changes in capacitance or vibration characteristics are indicative of one or more of heart rate, breathing rate and temperature of the user. In these embodiments, the integrated circuitry is configured to confirm the identity of the user based on at least one of the heart rate, the breathing rate and the temperature of the user. Further, in instances where the single touch implement is a user's palm, and the changes in capacitance or vibration characteristics are indicative of one or more of heart rate, breathing rate and temperature of the user, the integrated circuitry is configured to confirm the identity of the user based on at least one of the heart rate, the breathing rate and the temperature of the user's palm.

The embodiments and specific applications discussed herein may be implemented in connection with one or more of the above-described aspects, embodiments and implementations, as well as with those shown in the appended figures.

Turning now to the figures, FIG. 1 shows an example array of elements/cells 100, consistent with various aspects of the present disclosure. As shown in FIG. 1, each element/cell 105 of the array of elements/cells 100 includes a flexible plate 110 anchored around the edges. In response to application of a touch/pressure, the flexible plate of one or more elements/cells 105 deflects, and the deflection is detected. The array of elements/cells 100 allows for pressure determination that can be applicable for a variety of applications. The array of elements/cells 100 are arranged such that the elements/cells 105 are deflected in response to ridges of a finger 115. In this manner, the array of elements/cells 100 determines a map of ridges or a fingerprint, and thus can be used for fingerprint authentication. As noted above, the array of elements/cells 100 can be spread across a larger area to provide for touch location determination on a transparent touch screen. In such an embodiment, the sensor structures are made from transparent material and metals to allow the passage of light.

Detection of the deflection can occur in a number of ways. As shown in FIG. 1, the capacitive sensing arrangement where each one of these element/cells 105 is formed as a capacitor. A first electrode 120 is provided on the top flexible portion of each element/cell 105, and a corresponding second electrode 125 is provided at the bottom of each element/cell 105.

In certain embodiments, detecting only the change in capacitance provides for touch inputs. Capacitance can be measured continuously (enabling sensing touch and hold), or non-continuous capacitance measurements can be performed. In certain embodiments, piezoresistors are fabricated over the flexible plate, and are used to measure and sense the deflection of each element/cell. Additionally, piezoelectric transducers can also be fabricated on the flexible plate to sense the deflection. Aspects of the present disclosure allow for determination of a real fingerprint shape rather than the pattern of light and dark that makes up the visual impression of a fingerprint with optical devices.

Each individual element/cell 105 is provided as a single electrical contact for individual pressure sensing in each element/cell 105. Additionally, addressing of the electrical contacts can be provided in a row-column format similar to a memory, to reduce the number of interconnects. In this manner, the single electrical contacts for each element/cell 105 can be provided to an integrated sensor-electronics chip such that the required circuitry for each element/cell 105 is fitted in the area for each element/cell 105.

Figure 2:
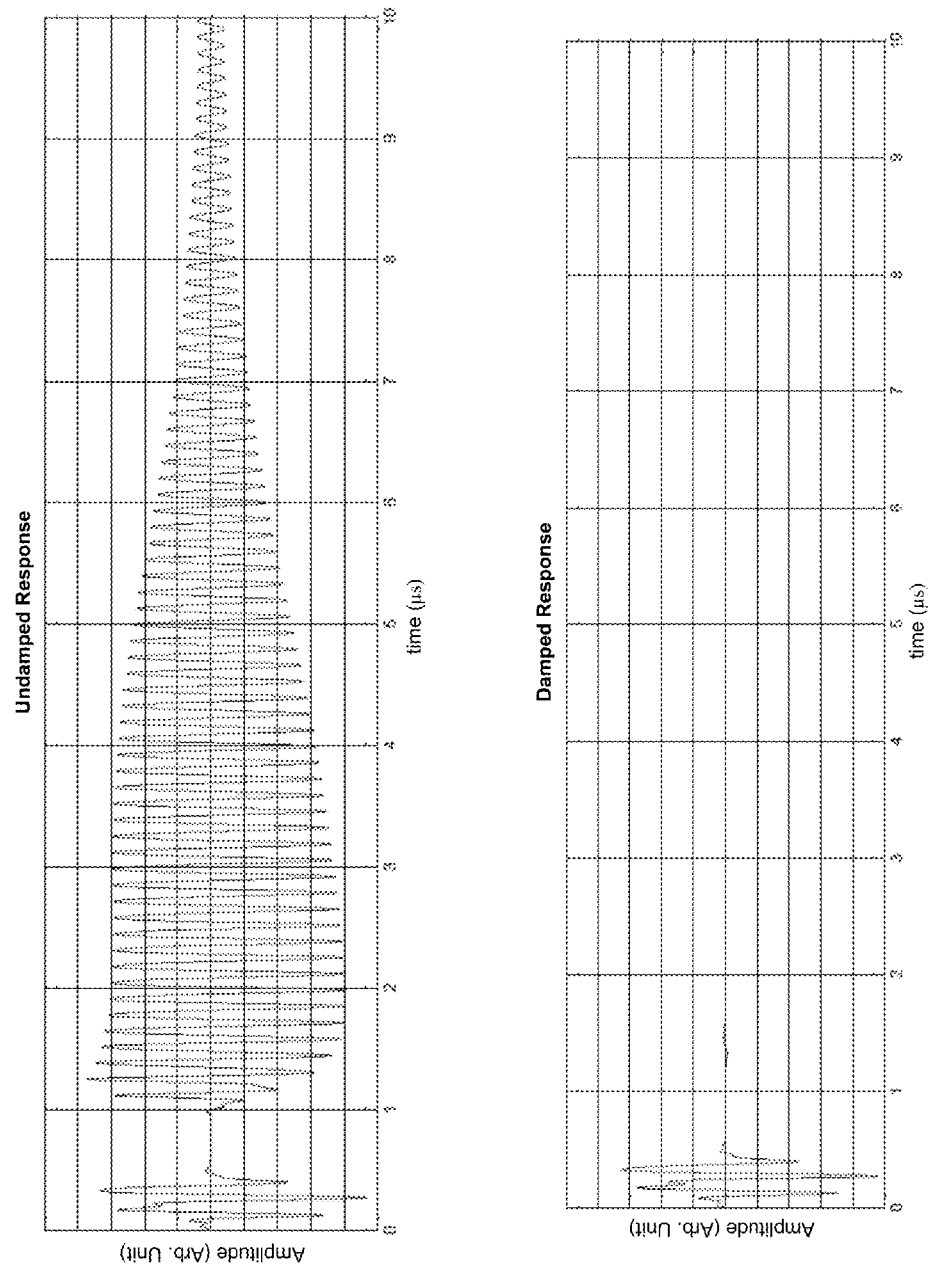
FIG. 2 shows an example undamped response of a touching implement on an example sensor array and an example damped response of a touching implement on an example sensor array, consistent with various aspects of the present disclosure.

FIG. 2 shows an example undamped response of a touching implement on an example sensor array and an example damped response of a touching implement on an example sensor array, consistent with various aspects of the present disclosure. In certain embodiments a plurality of sensor cells is constructed as capacitors. The touch sensing mechanism is based on a "loading" effect. For instance, a vibration in the flexible plate of one of these capacitor elements continues for a certain amount of time depending on several parameters. One of these parameters is the "load" the flexible plate sees (the medium in which the plate vibrates). If the load is air (e.g., in the case of no touch present or finger valley), this vibration will be most pronounced and would last for some time. However, if the plate is damped (e.g., in the case of a touch present or finger ridge) the vibration would die out much faster. This phenomenon can be used to detect a touch or for fingerprinting. If the sensor is undamped (e.g., by a finger valley), the response would ring (the upper graph shown in FIG. 2); if it is damped (e.g., by a finger ridge) the response would not show ringing (the bottom graph shown in FIG. 2). As noted above, the initial pulse that is similar in both cases is the excitation pulse effect. The presence or absence of vibration after 1 μs is an indication of no touch (finger valley) or touch (finger ridge), respectively.

Figure 3:
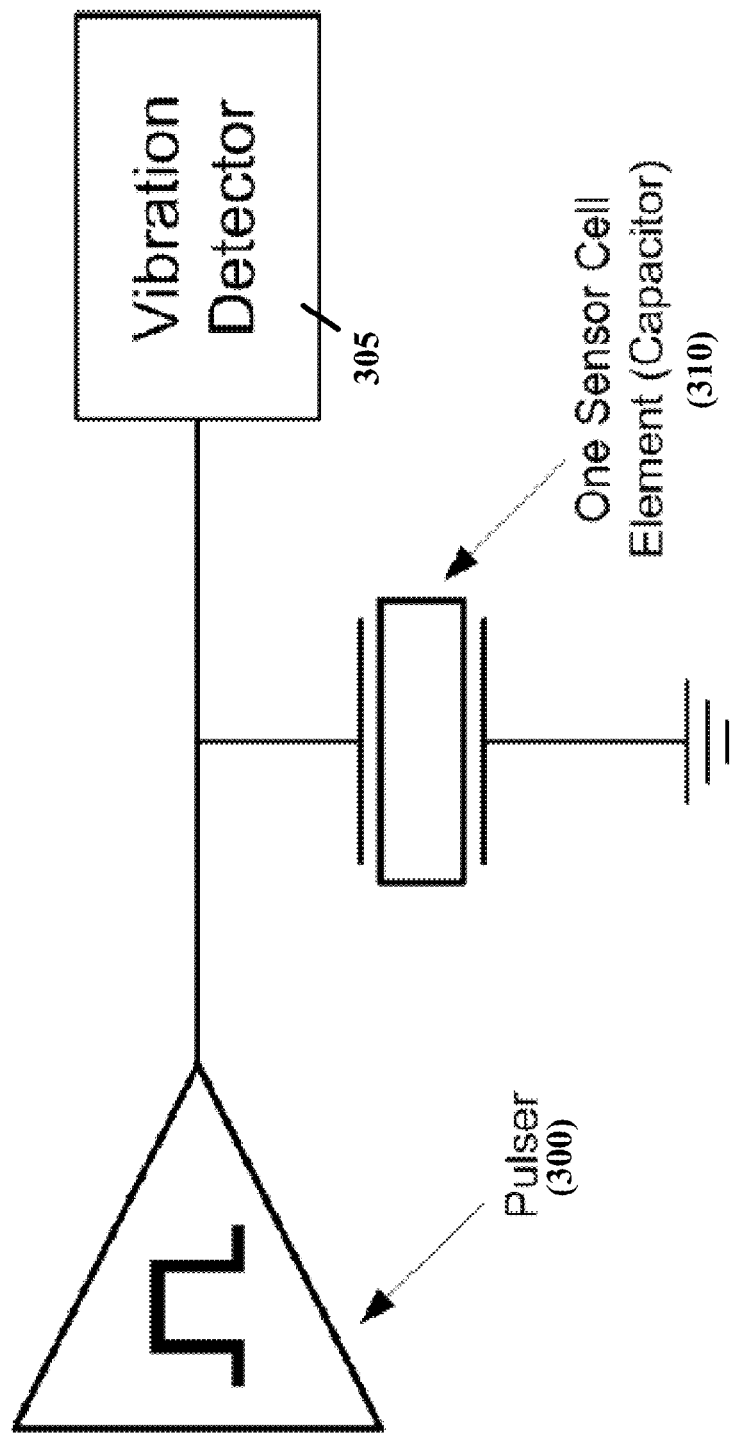
FIG. 3 shows example electronics that can implement with a sensor array, consistent with various aspects of the present disclosure.

FIG. 3 shows example electronics that can implement with a sensor array, consistent with various aspects of the present disclosure. The example electronics to implement this sensing mechanism as shown in FIG. 3 are composed of a pulser 300 and vibration detection circuitry 305 for each capacitor element 310. The pulser 300 excites the capacitor element 310 and, after some time, the vibration detection circuitry 305 searches for the vibration. The capacitor could be biased with a DC voltage so that the vibration would generate a current that can be sensed.

The vibration detection circuitry 305 can be implemented by way of an amplifier configured to detect or sense the current and convert the sensed current to a voltage. In such an embodiment, the amplifier is followed by a peak voltage detector, the output of which can be compared to one or more reference voltages to measure vibration and/or to indicate the presence or absence of vibration relative to the one or more reference voltages.

Various aspects of the present disclosure are also directed toward use of a pressure sensor or array of pressure sensors for biometric-type applications. For instance, heart rate can be determined by utilizing an array of pressure sensors, consistent with various aspects of the present disclosure. In certain embodiments, a single cell of an array of pressure-sensor cells (the array together being provided, for instance, for a fingerprint sensor or for a touch screen apparatus) can be used to determine heart rate of a person that touches the array of pressure-sensor cells. In other instances, a separate pressure-sensor cell, consistent with various aspects of the present disclosure, can be provided along with an array of pressure-sensor cells in an apparatus (e.g., fingerprint sensor or for a touch screen). This separate pressure-sensor cell can be configured to determine heart rate of a person contacting the apparatus. In both instances, the pressure-sensor cell that measures heart rate records an AC capacitance change over time. The waveform produced as a result of the measurement is processed to calculate the heart rate. With every heartbeat a mechanical pulse will be launched that originates from the heart and goes all over the body. This mechanical pulse that results from the heartbeat is visible in the recorded waveform. Blood vessels expand and contract in response to blood flow with every heartbeat, therefore, this expansion and contraction is displayed in the recorded waveform. Additionally, the heart rate variability (HRV), which is important for health metrics, can be measured by determining the heart rate over an extended period of time. Further, breathing rate can also be deduced from the recorded waveform due to the direct relationship between breathing rate and heart rate.

Moreover, tracks of the blood vessels in the fingers can be identified as a buried fingerprint due to pressure sensing of the heart rate. This feature enables detection of individual signature even if the fingerprint is erased or removed. Further, electrical response of the heart can be measured using an additional sensor (e.g., 1-lead Echocardiogram [ECG]). This by itself could be used to measure the heart rate and HRV in addition to other information in an ECG signal. This can be combined with mechanical pulse measurement, as discussed above, to calculate the time delay between the electrical indication of the heartbeat and the arrival of the mechanical pulse at the fingertip. This time delay can be an indicator of the cardiac and vascular health.

Various aspects of the present disclosure are also directed toward coupling of a temperature sensor with an apparatus having a pressure sensor or array of pressure sensors, consistent with various aspects of the present disclosure. For example, the temperature sensor (e.g., thermistor, thermocouple) integrated into the apparatus will determine temperature of a person that touches the array of pressure-sensor cells based on the fingertip contacting any position on the touching-surface of the apparatus.

Certain aspects of the present disclosure are also directed toward use of a pressure sensor or array of pressure sensors for biomodality or biometric (e.g., security) applications. For instance, the aspects of the present disclosure described above with respect to temperature, heart rate, and breathing rate, for example, allow for a 2-3 biomodality fingerprint determination. Measuring one or more of these aspects confirms the normalcy of a person that touches any position on the touching-surface of an apparatus that includes an array of pressure-sensor cells. This allows for determination that a live-being is contacting the apparatus rather than an attempted forgery (e.g., digit removal).

Various aspects of the present disclosure are also directed toward a handheld device (e.g., smartphone, tablet computer) that includes a pressure sensor or array of pressure sensors. Instead of utilizing an authentication/locking method of typing in a password or key, the pressure sensor or array of pressure sensors provides for fingerprint identification (as noted above). In this manner, the array of pressure sensors would also be used for the touch screen portion of the handheld device (e.g., smartphone, tablet computer). Further, a user of the handheld device could conduct health checks such as determining heart rate and breathing rate due to the health monitoring applications (as discussed above) that are provided by use of the array of pressure sensors, consistent with various aspects of the present disclosure. Similarly, an array of pressure sensors can be provided for as an apparatus, for example, directed toward other security purposes such as keyless entry to a house, office, car (e.g., an environment where a key or cardkey are used for access) or systems as security against theft and use by others. Additionally, applications provided on a smartphone can be integrated with the measurements taken by the pressure sensor or array of pressure sensors. In this manner, depending on the heart rate or breathing rate of a user, an application on the smartphone can be opened (such as a health monitoring software) or aspects of the application can be prompted (such as presenting a prompt for the user to consult a physician based on an irregular breathing rate or heart rate).

Various aspects of the present disclosure are directed toward an array of pressure sensors that are provided as a flexible and/or curved touching surface. For example, the array of pressure sensors can be provided such that the touching surface curves or wraps around the contour of the finger) to provide authentication and to read the fingerprint on a larger area around the fingertip without rolling the finger over the sensor. In other embodiments, the touching surface can be permanently curved (e.g., not necessarily flexible in its final form) to conform to the geometry of a certain device. For example in smart guns, one can imagine curved sensors embedded on the handle.

Various aspects of the present disclosure are also directed toward touch-screen display differentiation for distinguishing an actual touch (e.g., in which partially-stored aspects of the finger are recognized) over a near/unintended touch. Vibration that results in capacitance change does not alter the character of the underdamped resonance of a plate of the pressure sensor, consistent with various aspects of the present disclosure. Near/unintended touch will start the sensor to interpret the change in the resonant behavior as touch, however, due to the ability to distinguish between general features of a fingerprint and temperature, heart rate and duration of contact, aspects of the present disclosure can also distinguish between an intended or unintended touch.

Various aspects of the present disclosure are directed toward an array of pressure sensors for ballistogram applications. Similar to the above-mentioned pulse wave detection, detecting the pulse wave arrival time at different positions of the finger allows for ballistogram applications. If a single cell is used at one location of the finger to assess ballistography, then the signal from a single cell is detected over time and filtered to identify the low frequency components that correspond to acceleration of push against the sensor due to the heart pulse, in a similar manner of detecting low frequency signals over the DC signal of a strain gauge, for example, in a bathroom scale. For instance, a pressure sensor or array of pressure sensors captures a signal indicative of the physical movement and/or mechanical output of the heart of a user. A second specific sensor type (e.g., ECG, accelerometer, geophone, displacement, electromyogram or video imaging device), provided with the apparatus, determines additional information about the captured signal, which may be indicative of noise and/or interference present in the ballistogram measurement, or of other characteristics of the user. A processor circuit uses the second sensor signal to process the captured signal, such as to filter or gate (e.g., weight or eliminate aspects of) a captured ballistocardiogram (BCG) recording, and provide user diagnostics.

Various aspects of the present disclosure utilize passive touch-event recognition (e.g., determining changes in DC capacitance). This can be useful in recognizing at least one of the above biomodalities. Further, other aspects of the present disclosure utilize active touch-event recognition, e.g., determining changes in DC or AC capacitance, in at least one of the above biomodalities. Such touch determination mechanisms can be used with the pressure-sensor cells, consistent with various aspects of the present disclosure. Such apparatuses include any of a variety of display types including liquid crystal displays (e.g., active matrix, passive matrix, etc.), cathode ray tubes (CRT), plasma displays, etc. Passive touch event recognition and active touch event recognition are discussed in further detail in U.S. Pat. No. 8,279,180 (see, e.g., FIG. 2), U.S. Pat. No. 8,390,411 (see, e.g., FIG. 7) and U.S. Pat. No. 5,943,043 (see, e.g., FIGS. 5-6), and U.S. Patent Application Publication 2009/0051671 (see, e.g., FIGS. 1-3) which are fully incorporated herein by reference regarding such related teachings. More particularly, these U.S. patent documents are incorporated by reference with regards to exemplary circuits for implementing passive touch event recognition and active touch event recognition schemes. In an active touch display implementation, for instance, mutual capacitance formed at locations on the display screen can be excited by transmitting pulses along an X-axis via one or more X lines of a conductive grid and responsive signals are processed along the y-axis of the grid via one or more Y lines.

Aspects of the present disclosure are also directed toward fabrication of an integrated sensor. For instance, the required electronics are fabricated using integrated circuit fabrication. The capacitor sensor part is then fabricated on top of the electronics. Subsequently, an insulation layer is provided on the electronics wafer that will be patterned to create sensor cavities. Next, a silicon on insulator (SOI) wafer (or similar wafer) is bonded to this wafer using a low-temperature bonding technique. Finally, handle and box layers of the SOI are removed, and left is an array built on top of the supporting electronics. In certain embodiments, the required circuitry for each capacitor can be implemented in the same area as one capacitor. For general information regarding integrated sensor fabrication, and for specific information regarding fabrication of plates, to which one or more embodiments may be directed, reference may be made to U.S. Pat. No. 8,402,831, which is fully incorporated herein by reference for such related teachings consistent with aspects of the instant disclosure and, more particularly with regards to exemplary methodology and materials for implementing SOI wafers and to low temperature bonding of plates to complementary-metal-oxide semiconductor (CMOS).

Various embodiments described above may be implemented together and/or in other manners. For example, while the illustrated array of pressure cells is described/illustrated using one example of how such an array would be implemented, it would be appreciated that other/more specific embodiments would include arrays of varying quantity and arrangement such as a two-dimensional array of a few-to-several cells for covering a target area (e.g., row-and-column (x-y-axes) arrangement where a relatively small amount of information is sensed) and arrays having more than two-dimensions such as with cells stacked on the x-y plane to form a third dimension along the Z-axis as would be useful for sensing regions of a finger as the regions curve upwardly and away from the x-y plane. In such multidimensional arrays, the arrangement of pressure sensors can be implemented using the contact surfaces that are flexible as well as stiff. Certain such embodiments can be implemented to use the sensing cell and related circuitry to take advantage of the manner in which the cells are arranged to engage. Further, one or more of the items depicted in the present disclosure can also be implemented separately or in a more integrated manner, as is useful in accordance with particular applications.

As illustrated herein, various circuit-based building blocks and/or modules may be implemented to carry out one or more of the operations and activities described herein shown in the block-diagram-type figures. In such contexts, these building blocks and/or modules represent circuits that carry out one or more of these or related operations/activities. For example, in certain of the embodiments discussed above (such as the pulser circuitry modularized as shown in FIG. 3), one or more blocks/modules are discrete logic circuits or programmable logic circuits configured and arranged for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Based upon the above discussion and illustrations, those skilled in the art will readily recognize that various modifications and changes may be made to the present invention without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present invention, including that set forth in the following claims.

What is claimed is:

1. An apparatus comprising:
    a pressure-sensor arrangement including a plate structure and a plurality or array of pressure-sensor cells, with the plate structure anchored around edges of the plurality or array of pressure-sensor cells;
    integrated circuitry communicatively coupled to the pressure-sensor arrangement and configured and arranged to provide capacitance and to sense pressure changes exhibited by changes in the capacitance or in vibration due to dampening, the integrated circuitry including separate signal paths for each of the plurality or array of pressure-sensor cells; and
    the plurality of pressure-sensor cells and the plate structure being configured and arranged to detect changes in capacitance or in vibration in the pressure-sensor arrangement due to dampening, via the separate signal paths, in response to a touch event at or near the plate structure as caused by a single touch, wherein the pressure-sensor arrangement is configured and arranged to include the separate signal paths for each of the respective pressure-sensor cells to provide an indication of the touch event at or near the plate structure.

2. The apparatus of claim 1, wherein the single touch is caused by a stylus having a plurality of surface irregularities at the tip of the stylus, and wherein the pressure-sensor arrangement is configured and arranged with the separate signal paths so that each of the respective pressure-sensor cells provides an indication of a change in pressure in response to the touch event at or near the plate structure in order to sense different ones of the plurality of surface irregularities.

3. The apparatus of claim 1, wherein the single touch is caused by a finger of a user, and the changes in capacitance are indicative of one or more of heart rate, breathing rate and temperature of the user.

4. The apparatus of claim 1, wherein the single touch is caused by a finger of a user, and the changes in capacitance are indicative of blood flow of the user.

5. The apparatus of claim 1, wherein the single touch is caused by a finger of a user, and the changes in capacitance are indicative of tracks of blood vessels of the finger.

6. The apparatus of claim 1, wherein the single touch is caused by a finger of a user, and the changes in capacitance are indicative of one or more of heart rate, breathing rate and temperature of the user, and the integrated circuitry is further configured and arranged to confirm identity of the user based on at least one of the heart rate, the breathing rate and the temperature of the user.

7. The apparatus of claim 1, further including a touch surface provided over the plurality of pressure-sensor cells and the plate structure, the touch surface being provided across an area at least sufficient to allow a single touch, including multiple fingers or a user's palm, to contact the touch surface.

8. The apparatus of claim 1, wherein the single touch is caused by at least one finger of a user, and the changes in capacitance are indicative of one or more of heart rate, breathing rate and temperature of the user, and the integrated circuitry is further configured and arranged to confirm identity of the user based on at least one of the heart rate, the breathing rate and the temperature of the user.

9. The apparatus of claim 1, wherein the single touch is caused by a user's palm, and the changes in capacitance are indicative of one or more of heart rate, breathing rate and temperature of the user, and the integrated circuitry is further configured and arranged to confirm identity of the user based on at least one of the heart rate, the breathing rate and the temperature of the user.

10. An apparatus comprising:
a pressure-sensor arrangement including a plate structure and a plurality or array of pressure-sensor cells, with the plate structure being anchored around edges of the plurality or array of pressure-sensor cells;
integrated circuitry communicatively coupled to the pressure-sensor arrangement and configured and arranged to sense pressure changes exhibited by changes in capacitance, the integrated circuitry including separate signal paths for each of the plurality or array of pressure-sensor cells; and
the plurality of pressure-sensor cells and the plate structure being configured and arranged to provide different changes in capacitance, via the separate signal paths, in response to a touch event at or near the plate structure as caused by a single touch, wherein the pressure-sensor arrangement is configured and arranged to include the separate signal paths for each of the respective pressure-sensor cells to provide an indication of a change in pressure in response to the touch event at or near the plate structure as caused by the single touch.

11. The apparatus of claim 10, wherein the single touch is a finger, and the pressure-sensor arrangement is configured and arranged to include at least several pressure-sensor cells wherein the separate signal paths for each of the respective pressure-sensor cells provides an indication of a change in pressure in response to the touch event at or near the plate structure in order to sense a plurality of ridges in the finger.

12. An apparatus comprising:
a pressure-sensor arrangement including a plate structure and a plurality or array of pressure-sensor cells;
integrated circuitry communicatively coupled to the pressure-sensor arrangement and configured and arranged to sense pressure changes exhibited by changes in capacitance, the integrated circuitry including separate signal paths for each of the plurality or array of pressure-sensor cells;
the plurality of pressure-sensor cells and the plate structure being configured and arranged to provide different changes in capacitance, via the separate signal paths, in response, to a touch event at or near the plate structure as caused by a single touch, with the plate structure anchored around edges of the plurality or array of pressure-sensor cells, and
a touch screen in which the plate structure is configured and arranged to deflect in response to a touch event.

13. The apparatus of claim 12, wherein the plate structure is further configured and arranged to detect sufficient ridges in a fingerprint for differentiating between ridge spacing along at least one direction.

14. The apparatus of claim 12, wherein the plate structure is further configured and arranged to detect sufficient ridges in a fingerprint for differentiating between ridge spacing along at least two directions.

15. An apparatus comprising:
a pressure-sensor arrangement including a plate structure and a plurality or array of pressure-sensor cells, with the plate structure anchored around edges of the plurality or array of pressure-sensor cells;
integrated circuitry communicatively coupled to the pressure-sensor arrangement and configured and arranged to sense pressure changes exhibited by changes in vibration characteristics, the integrated circuitry including separate signal paths for each of the plurality or array of pressure-sensor cells; and
the plurality of pressure-sensor cells and the plate structure being configured and arranged to provide different changes in vibration characteristics, via the separate signal paths, in response to a touch event at or near the plate structure as caused by a single touch, wherein the changes in vibration characteristics are indicative of one or more of heart rate of a user, breathing rate of the user, physical touch by the user and temperature of the user, and the integrated circuitry is further configured and arranged to generate a signal representing the changes in vibration characteristics.

16. The apparatus of claim 15, wherein the single touch is caused by a finger of a user.

17. The apparatus of claim 15, wherein the single touch is caused by at least one finger of a user, and the changes in vibration characteristics are indicative of one or more of heart rate, breathing rate and temperature of the user, and the integrated circuitry is further configured and arranged to confirm identity of the user based on at least one of the heart rate, the breathing rate and the temperature of the user.

18. The apparatus of claim 15, wherein the signal representing the changes in vibration characteristics includes information for identifying the user.

19. A method comprising:
providing a pressure-sensor arrangement including a plate structure and a plurality or array of pressure-sensor cells, with the plate structure being anchored around edges of the plurality or array of pressure-sensor cells;

providing integrated circuitry communicatively coupled to the pressure-sensor arrangement and configured and arranged to sense pressure changes exhibited by changes in capacitance or vibration characteristics, the integrated circuitry including separate signal paths for each of the plurality or array of pressure-sensor cells; and in response to a touch event at or near the plate structure as caused by a single touch, determining different changes in capacitance or vibration characteristics, via the separate signal paths and the plurality of pressure-sensor cells and the plate structure, wherein the single touch is caused by at least one finger of a user, and the changes in vibration characteristics are indicative of one or more of heart rate, breathing rate and temperature of the user, and the integrated circuitry is further configured and arranged to generate a signal representing the changes in vibration characteristics.

20. The method of claim 19, wherein the integrated circuitry is further configured and arranged to confirm identity of the user based on at least one of the heart rate, the breathing rate and the temperature of the user.

* * * * *